United States Patent [19]

Reichelt et al.

[11] 4,186,198

[45] Jan. 29, 1980

[54] CHEMICAL COMPOUNDS

[75] Inventors: Karl-Ludwig Reichelt; Olav E. Trygstad, both of Oslo, Norway

[73] Assignee: Nyegaard & Co. A/S, Olso, Norway

[21] Appl. No.: 939,970

[22] Filed: Sep. 6, 1978

[30] Foreign Application Priority Data

Sep. 6, 1977 [GB] United Kingdom ............... 37194/77

[51] Int. Cl.² ..................... A61K 37/00; C07C 103/52
[52] U.S. Cl. .............................. 424/177; 260/112.5 R
[58] Field of Search .................. 424/177; 260/112.5 R

[56] References Cited
PUBLICATIONS

Pettit, Synthetic Peptides 4, pp.192–193 (1977).

*Primary Examiner*—Delbert R. Phillips
*Attorney, Agent, or Firm*—Bacon & Thomas

[57] ABSTRACT

The invention relates to L-pyroglutamyl-L-seryl-glycyl-glycine amide which possesses the ability to increase serum testosterone levels and is thus of interest in promoting anabolism and other hormonal effects associated with testosterone. Process for the preparation of the compound and pharmaceutical compositions containing the compound as active ingredient are described and exemplified.

11 Claims, No Drawings

CHEMICAL COMPOUNDS

The present invention relates to a novel peptide as well as to processes for its preparation.

The present invention is based upon the discovery of a novel peptide found in the urine of patients suffering from congenital generalized lipodystrophy, which peptide possesses the ability to increase serum testosterone levels and is thus of interest in promoting anabolism and the other hormonal effects associated with testosterone. This peptide has been found to be L-(pyro)-glutamyl-L-seryl-glycyl-glycine amide.

Thus according to one feature of the present invention there is provided the compound of the general formula:

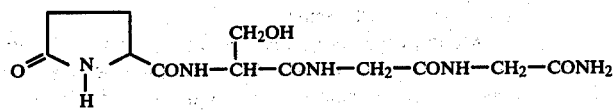

(I)

(wherein the pyroglutamyl and seryl moieties are of the L-series).

According to a further feature of the present invention there is provided a process for the preparation of the compound of formula I which comprises deprotecting a compound of the formula

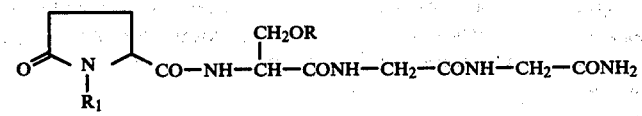

(II)

(wherein the pyroglutamyl and seryl moieties are each of the L-series and $R_1$ represents a hydrogen atom or an amine protecting group, and R represents a hydrogen atom or a hydroxyl protecting group with the proviso that at least one of R and $R_1$ represents a protecting group) whereby a compound of formula I is obtained.

As indicated the compound of formula II may be only partially protected, only one of R and $R_1$ then being in protected form; such compounds may be prepared by selective partial deprotection of a compound of formula II in which both of R and $R_1$ are in protected form or they may be synthesised in partially protected form. In particular R will commonly be hydrogen.

Where, however, a compound of formula II is used in which R and $R_1$ each represent a protecting group it is advantageous to remove both the protecting groups simultaneously.

A compound of formula I or formula II may, for example, be prepared from a compound of the formula:

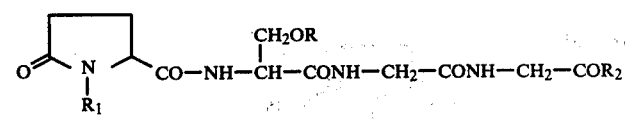

(Ia)

(wherein $R_1$ represents a hydrogen atom or an amino protecting group, $R_2$ represents a hydroxyl group or a carboxylic acid activating or protecting group and R represents a hydrogen atom or a hydroxyl protecting group) by amidation, which may, for example, be effected in a single step or in two or more stages. Thus, for example, a compound of formula Ia in which $COR_2$ represents an esterified carboxyl group may be reacted directly with ammonia to form the required amide group. Alternatively, when $COR_2$ represents a free carboxyl group this may be activated for example by formation of a terminal grouping of the formula

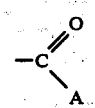

where A represents an atom or group removable as an anion, e.g. an atom or group as hereinafter defined for X, such as an alkoxy or acyloxy group (e.g. with up to 6 carbon atoms) or a halogen atom e.g. chlorine and the activated compound thus obtained may then be reacted with ammonia to yield the desired amide. When $COR_2$ represents a protected carboxyl group, this may be deprotected and activated as above prior to reaction with ammonia.

A compound of formula I or II or a compound of formula Ia in which $R_2$ represents a hydroxy or carboxyl protecting group may, for example, be prepared by reacting a compound of the formula:

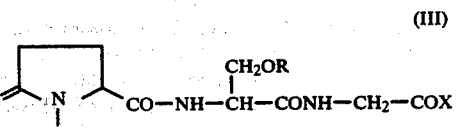

(III)

(wherein the pyroglutamyl and seryl moieties are each of the L-series, $R_1$ represents a hydrogen atom or an amine protecting group, R represents a hydrogen atom or a hydroxyl protecting group and X represents a hydroxyl group or a carboxylic acid activating substituent) with a compound of the formula:

$$NH_2-CH_2-COR_2'$$  (VI)

(wherein $R_2'$ represents a hydroxyl or amino group or a carboxyl protecting group) whereby said compound of formula I, Ia or II is obtained.

A compound of formula III is preferably used in which $R_1$ represents an amine protecting group and/or X represents a carboxylic acid activating group, R being, in general, preferably hydrogen. Where it is desired to prepare a compound of formula Ia in which $R_2$ represents a hydroxyl group, a compound of formula IV is preferably used in which $R_2'$ represents a carboxyl protecting group. Where, however, it is desired to prepare a compound of formula I a compound of formula IV is preferably used in which $R_2'$ represents an amino group.

Similarly a compound of formula I or II or a compound of formula Ia in which $R_2$ is a hydroxyl or carboxyl protecting group may, for example, be prepared by reacting the L-isomer of a compound of the formula:

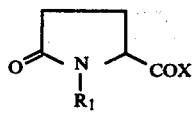
(V)

(wherein $R_1$ represents a hydrogen atom or an amine protecting group and X represents a hydroxyl group or a carboxylic acid activating substituent) with the L-isomer of a compound of the formula:

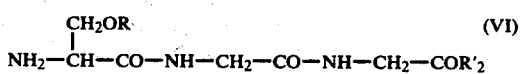
(VI)

(wherein $R_2'$ and R have the above meanings) whereby a compound of formula I or II is obtained.

A compound of formula V is preferably used in which $R_1$ represents an amine protecting group and/or X represents a carboxylic acid activating substituent. Where it is desired to prepare a compound of formula Ia in which $R_2$ represents a hydroxyl group a compound of formula VI is preferably used in which $R_2'$ represents a carboxyl protecting group. Where however it is desired to prepare a compound of formula I a compound of formula VI is preferably used in which $R_2'$ represents an amino group; in general R is preferably hydrogen.

A compound of formula III as hereinbefore defined (wherein X represents a carboxylic acid activating substituent) may, for example, be prepared by reacting, the L,L-isomer of a compound of formula III (wherein X represents a hydroxyl group) by methods known per se to form a compound of formula III wherein X represents a carboxylic acid activating group.

A compound of formula III as hereinbefore defined (wherein X represents a hydroxyl group) may, for example, be prepared by reacting a compound of the formula:

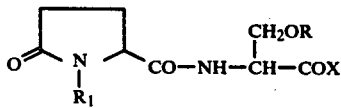
(VII)

(wherein the pyroglutamyl and seryl moieties are each of the L-series, and $R_1$, R and X have the above meanings) with a compound of the formula:

$NH_2—CH_2—COR_2''$ (VIII)

(wherein R" represents a hydroxyl group or a carboxyl protecting group) and where a compound of formula VIII is used in which $R_2''$ represents a carboxyl protecting group, converting the compound thus obtained into a compound of formula III as hereinbefore defined (wherein X represents a hydroxyl group) by deprotection of the said carboxyl protecting group.

It is preferred to use a compound of formula VII in which $R_1$ represents an amine protecting group and/or in which X represents a carboxylic acid activating substituent. It is also preferred to use a compound of formula VIII in which $R_2''$ represents a carboxyl protecting group, which group is then removed after the reaction to form a compound of formula III in which X represents a hydroxyl group.

The compound of formula VII (wherein X represents a carboxylic acid activating group) may, for example, be prepared by reacting the L,L-isomer of a compound of formula VII (wherein X represents a hydroxyl group) by methods known per se to form a compound of formula VII (wherein X represents a carboxylic acid activating substituent).

A compound of formula VII (wherein X represents a hydroxyl group) may, for example, be prepared by reacting the L-isomer of a compound of the formula:

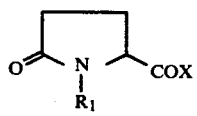
(V)

(wherein $R_1$ represents a hydrogen atom or an amine protecting group and X represents a hydroxyl group or a carboxylic acid activating group) with the L-isomer of a compound of the formula:

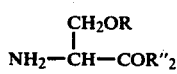
(IV)

(wherein $R_2''$ and R have the above meanings) and where a compound of formula IV is used in which $R_2'$ represents a carboxyl protecting group, converting the compound thus obtained into a compound of formula VII (wherein X represents a hydroxyl group) by deprotection of the said carboxyl protecting group.

It is preferred to use a compound of formula V in which $R_1$ represents an amine protecting group and/or in which X represents a carboxylic acid activating substituent. It is also preferred to use a compound of formula IV in which $R_2'$ represents a carboxyl protecting group, which group is then removed after the reaction to form a compound of formula VII in which X represents a hydroxyl group.

A compound of formula III as hereinbefore defined (wherein X represents a hydroxyl group) may, for example also be prepared by reacting the L-isomer of a compound of the formula:

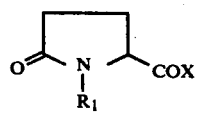
(V)

(wherein $R_1$ represents a hydrogen atom or an amine protecting group and X represents a hydroxyl group or a carboxylic acid activating substituent) with a compound of the formula

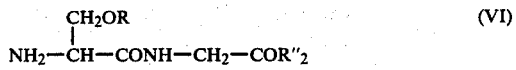

$$\text{NH}_2\text{—CH—CONH—CH}_2\text{—COR}''_2 \quad \text{(VI)}$$

(wherein the seryl moiety is of the L-series and $R_2''$ and $R_3$ have the above meanings) and where a compound of formula IX is used in which $R_241$ represents a carboxyl protecting group, converting the compound thus obtained into a compound of formula III (wherein X represents a hydroxyl group) by deprotection of the said carboxyl protecting group.

It is preferred to use a compound of formula V in which $R_1$ represents an amine protecting group and/or in which X represents a carboxylic acid protecting group. It is also preferred to use a compound of formula IX in which $R_2''$ represents a carboxylic acid protecting group, which group is then removed after the reaction to form a compound of formula III in which X represents a hydroxyl group.

A compound of formula IX as hereinbefore defined may, for example, be prepared by removal of the amine protecting group from a compound of the formula:

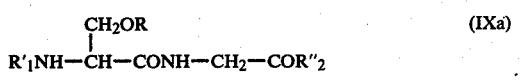

$$\text{R}'_1\text{NH—CH—CONH—CH}_2\text{—COR}''_2 \quad \text{(IXa)}$$

(wherein the seryl moiety is of the L-series, $R_1'$ represents an amine protecting group and R and $R_2''$ have the above meaning) whereby a compound of formula IX is obtained.

A compound of formula IX or IXa as hereinbefore defined may, for example, be prepared by reacting the L-isomer of a compound of the formula:

$$\text{R}_1\text{NH—CH—COX} \quad \text{(X)}$$

(wherein $R_1$ represents a hydrogen atom or an amine protecting group, X represents a hydroxyl group or a carboxylic acid activating substituent and R has the above meaning) with a compound of the formula:

$$\text{NH}_2\text{—CH}_2\text{—COR}_2'' \quad \text{(VIII)}$$

(wherein $R_2''$ has the above meaning).

It is preferred to use a compound of formula X in which $R_1$ represents an amine protecting group and/or in which X represents a carboxylic acid activating substituent. It is also preferred to use a compound of formula VIII in which $R_2''$ represents a carboxylic acid protecting group, which group is then removed after the reaction to form a compound of formula III in which X represents a hydroxyl group.

A compound of formula VI as hereinbefore defined may for example be prepared by removal of the amine protecting group from a compound of the formula:

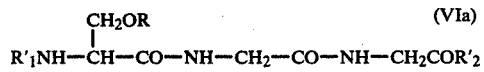

$$\text{R}'_1\text{NH—CH—CO—NH—CH}_2\text{—CO—NH—CH}_2\text{COR}'_2 \quad \text{(VIa)}$$

(wherein the seryl moiety is of the L-series and $R_1'$ represents an amine protecting group and $R_2'$ and R have the above meanings) whereby a compound of formula VI is obtained.

The compound of formula VI or VIa may, for example, be prepared by reacting a compound of the formula:

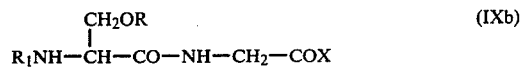

$$\text{R}_1\text{NH—CH—CO—NH—CH}_2\text{—COX} \quad \text{(IXb)}$$

(wherein the seryl moiety is of the L-series, $R_1$ and R have the above meanings and X represents a hydroxyl group or a carboxylic acid activating substituent with a compound of the formula:

$$\text{NH}_2\text{—CH}_2\text{—COR}_2' \quad \text{(IV)}$$

(wherein $R_2'$ has the above meaning) whereby a compound of formula VI or VIa is obtained.

It is preferred to use a compound of formula IXb in which $R_1$ represents an amine protecting group, which group may be removed after the reaction. It is also preferred to use a compound of formula IXb in which X represents a carboxylic acid activating substituent. Where it is desired to prepare a compound of formula Ia in which $R_2$ represents a hydroxyl group a compound of formula IV is preferably used in which $R_2'$ represents a carboxyl protecting group. Where, however, it is desired to prepare a compound of formula I a compound of formula IV is preferably used in which $R_2'$ represents an amino group.

The compound of formula IXb (wherein X represents a carboxylic acid activating substituent) may, for example, be prepared by reacting a compound of formula IXb (wherein X represents a hydroxyl group) by methods known per se to form a compound of formula IXb (wherein X represents a carboxylic activating substituent). A compound of formula IXb (wherein X represents a hydroxyl group) may, for example, be prepared by reacting the L-isomer of a compound of the formula:

$$\text{R}_1\text{—NH—CH—COX} \quad \text{(X)}$$

(wherein $R_1$ represents a hydrogen atom or an amine protecting group, X represents a hydroxyl group or a carboxylic acid activating substituent and R has the above meaning) with a compound of the formula:

$$\text{NH}_2\text{—CH}_2\text{—COR}_2'' \quad \text{(VIII)}$$

(wherein $R_2''$ has the above meaning) and where a compound of formula VIII is used in which $R_2''$ represents a carboxyl protecting group, converting the compound thus obtained into a compound of formula IXb (wherein X represents a hydroxyl group) by deprotection of the said carboxyl protecting group.

It is preferred to use a compound of formula X in which $R_1$ represents an amine protecting group and/or in which X represents a carboxylic acid activating substituent. It is also preferred to use a compound of formula VII in which $R_2$ represents a carboxyl protecting group, which group is then removed after the reaction to form a compound of formula IXb in which X represents a hydroxyl group.

A compound of formula VI or VIa may also, for example, be prepared by reacting the L-isomer of a compound of the formula:

$$\underset{R_1NH-CH-COX}{\overset{CH_2OR}{|}} \quad (X)$$

(wherein $R_1$ represents a hydrogen atom or an amine protecting group, X represents a hydroxyl group or a carboxylic acid activating substituent and R has the above meaning) with a compound of the formula:

$$NH_2-CH_2CONH-CH_2-COR_2' \quad (XI)$$

(wherein $R_2'$ has the above meaning) whereby a compound of formula VI or VIa is obtained.

It is preferred to use a compound of formula X in which $R_1$ represents an amine protecting group and/or in which X represents a carboxylic acid activating substituent. Where it is desired to prepare a compound of formula Ia in which $R_2$ represents a hydroxyl group, a compound of formula IV is preferably used in which $R_2'$ represents a carboxyl protecting group. Where, however, it is desired to prepare a compound of formula I a compound of formula XI in which $R_2'$ represents an amino group is preferably used.

The compound of formula XI as hereinbefore defined may, for example, be prepared by removal of the amine protecting group from a compound of the formula:

$$R_1'NH-CH_2-CONH-CH_2-COR_2' \quad (XIa)$$

(wherein $R_1'$ represents an amine protecting group and $R_2'$ has the above meaning) whereby a compound of formula XI is obtained.

The compound of formula XI or XIa may, for example, be prepared by reacting a compound of the formula:

$$R_1NH-CH_2-COX \quad (XII)$$

(wherein $R_1$ has the above meaning and X represents a hydroxyl group or a carboxylic acid activating substituent) with a compound of the formula:

$$NH_2-CH_2-COR_2' \quad (IV)$$

(wherein $R_2'$ represents a hydroxyl or amino group or a carboxyl protecting group) whereby a compound of formula XI or XIa is obtained.

It is preferred to use a compound of formula XII in which $R_1$ represents an amine protecting group and/or in which X represents a carboxylic acid activating substituent. Where it is desired to prepare a compound of formula I in which R represents a hydroxyl group, a compound of formula IV is preferably used in which $R_2'$ represents a carboxyl protecting group. Where, however, it is desired to prepare a compound of formula I, a compound of formula IV in which $R_2'$ represents an amino group is preferably used.

As stated above, where it is desired to prepare a compound of formula I it is preferred to use a compound of formula IV in which $R_2'$ represents an amino group. It will be appreciated, however, that where $R_2'$ or $R_2''$ represent a hydroxyl group or a carboxyl protecting group in any of the compounds of formulae II, VI, VIa, XI or XIa, the said group $R_2'$ or $R_2''$ may be converted into an amino group at any stage of the above-described reaction sequence using the methods described above.

Where in any of the above reactions a mixture of products is obtained, the desired product may be isolated from the reaction mixture by conventional methods known per se.

It will be appreciated that the compounds of the present invention may, if desired, be prepared according to the processes herein described using the solid-phase method of peptide synthesis. In such a method the carboxyl protecting group of the C-terminal amino acid may be in the form of a resin.

The compounds of formula IV, V, VIII, X and XII are either readily available starting materials or may readily be derived from available starting materials according to methods well known in the literature.

A wide choice of protecting and activating groups as well as procedures for protecting, activating and coupling amino acids are known and are exemplified in Schroder, E., and Lubke, K., The Peptides, Vols. 1 or 2, Academic Press, New York and London, 1965 and 1966; Pettit, G. R., Synthetic Peptides, Vols. 1–4, Van Nostrand, Reinhold, New York 1970, 1971, 1975 and 1976, Houben-Weyl, Methoden der Organischem Chemie, Synthese von Peptiden, Band 15, Georg Thiene Verlag, Stuttgart 1974; and Amino Acids, Peptides and Proteins, Vol. 4–8, The Chemical Society, London 1972, 1974, 1975 and 1976.

Thus, for example amine protecting groups which may be employed include the carbobenzoxy (hereinafter also designated Cbz or Z), t-butoxycarboxyl (hereinafter also designated BOC) and acyl groups such as, for example, an acetyl group or a formyl group.

Carboxyl protecting groups which may, for example be employed include readily cleaved ester groups such as benzyl (hereinafter also designated Bzl), p-nitrobenzyl or t-butyl groups.

Hydroxyl protecting groups which may, for example, be employed include acyloxy groups such as acetoxy or trichloroacetoxy and readily cleaved ether groups such as tetrahydropyranyloxy groups and tri-hydrocarbyl-silyloxy groups.

Carboxylic acid activating substitutents which may, for example, be employed include mixed anhydrides, azides or activated esters such as for example the p-nitrophenyl ester, 2,4,5-trichlorophenyl ester, or N-hydroxysuccinimidyl ester.

It will be appreciated that a wide range of other such groups exist as, for example, detailed in the above-mentioned literature references and the use of all such groups in the hereinbefore described processes fall within the scope of the present invention.

The processes of the present invention will generally be effected by the use of L-pyroglutamyl and L-seryl starting materials in the absence of the D-isomers thereof. It is thus desirable to conduct the reactions under conditions which avoid racemisation in order to avoid the need for a resolution process at the end of the total reaction sequence.

It is also possible, but less convenient, to use racemic pyroglutamyl and seryl starting materials and include one or more optical resolution stages.

Carboxyl protecting groups may be introduced by conventional methods e.g. by reaction with a suitable esterifying reagent, for example an alcohol such as benzyl or p-nitrobenzyl alcohol in the presence of acid, e.g. p-toluenesulphonic acid.

Amine protecting groups may be introduced by conventional methods e.g. by reaction with suitable acid halides such as carbobenzoxyl chloride or pivaloyl chloride, or acid anhydrides such as acetic anhydride.

Hydroxyl protecting groups may be introduced by conventional methods such as acylation, e.g. using an appropriate anhydride or acid halide, reaction with dihydropyran or reaction with a tri-hydrocarbylsilyl halide.

In general it is convenient to effect the coupling reactions at low temperatures, for example, −20° C. up to ambient temperature, conveniently in a suitable solvent system, for example, tetrahydrofuran, dioxan, dimethylformamide, methylene chloride or a mixture of these solvents.

The coupling of free amino and carboxyl groups may, for example, be effected using dicyclohexylcarbodiimide (DCC). Another coupling agent which may, for example, be employed is N-ethoxycarbonyl-2-ethoxy-1,2-dihydroquinoline.

Activation of carboxyl groups may for example be effected by conversion of the acid to a reactive derivative, e.g. the acid anhydride, which may for example be prepared by the use of ethyl or isobutyl chloroformate. Acylation of another amino acid with a mixed anhydride or other activated carboxyl derivative may be effected by methods conventional in peptide synthesis.

Usually, the reaction product after the coupling step contains one or more protecting group(s). If desirable, these can be removed, for example in a selective way. Thus it is possible to remove only certain groups, keeping others intact during the subsequent reaction(s).

As stated above a wide range of procedures exist for removing amine, hydroxyl and carboxyl protecting groups. Thus, for example an amine protecting group may be removed by acidolysis, hydrogenolysis, treatment with dilute ammonium hydroxide, treatment with sodium, treatment with sodium amide, treatment with hydrazine, or enzymatic hydrolysis with, for example, leucineaminopeptidase. Methods which are of interest also include treatment with anhydrous hydrogen bromide for example in glacial acetic acid, treatment with trifluoroacetic acid and catalytic hydrogenation.

Thus carbobenzoxy and t-butoxy carbonyl groups may be removed, for example, using anhydrous hydrogen bromide conveniently in the presence of glacial acetic acid or using trifluoroacetic acid conveniently in the presence of concentrated hydrochloric acid; acyl groups may for example be removed by conventional hydrolysis with acid or by enzymic hydrolysis as described above.

The removal of carboxyl protecting groups may, for example, be effected by saponification, acidolysis, hydrogenolysis or enzymatic hydrolysis. Thus, for example, saponification may be effected with an alkali metal hydroxide conveniently in the presence of water, an alcohol and/or acetone. Acidolysis may, for example, be effected by the use of anhydrous hydrogen bromide or trifluoroacetic acid and hydrogenolysis may, for example, be effected by catalytic hydrogenation e.g. by the use of palladium on carbon, conveniently 10% palladium on charcoal. Enzymatic hydrolysis may, for example, be effected by the use of leucineaminopeptidase. Thus, for example, benzyl and p-nitrobenzyl groups may be removed by hydrogenolysis and t-butyl groups may, for example, be removed by saponification.

Hydroxyl protecting groups may be removed, for example, by acidolysis, acid or alkaline hydrolysis, hydrogenolysis or enzymatic hydrolysis.

Amine, hydroxyl and carboxyl protecting groups may, for example, be removed simultaneously by acidolysis, alkaline hydrolysis, hydrogenolysis, treatment with sodium or sodium amide or by enzymatic hydroslysis. Such methods include treatment with hydrogen bromide conveniently in the presence of glacial acetic acid and treatment with an alcohol conveniently containing dissolved dry hydrogen chloride.

One method of selective deprotection, is for example, catalytic hydrogenation, conveniently using palladium on, for example, carbon as the catalyst and conveniently in the presence of a solvent e.g. water, methanol, dioxan, acetic acid or t-butanol. This method removes, for example, the carbobenzoxy group, but leaves the t-butoxycarbonyl or an acyl group intact.

The reaction product can then be isolated and purified by known methods, such as for example extraction, crystallization or chromatography (e.g. thin layer or column). It may be advantageous to isolate and purify the desired peptide product by salt formation (e.g. hydrochloride, hydrobromide or dicyclohexylamine salt formation). Intermediates and the end products may, for example, be characterized by chromatographic parameters (purity control), optical rotation and especially spectroscopic data.

According to a still further feature of the present invention there are provided pharmaceutical compositions comprising as active ingredient at least one compound of formula I as hereinbefore defined or a physiologically compatible salt thereof in association with a pharmaceutical carrier or excipient. The compositions according to the invention may be presented, for example, in a form suitable for oral, parenteral or rectal administration.

As used herein, the term "pharmaceutical" includes veterinary applications of the invention.

The compounds according to the invention may be presented in the conventional pharmacological forms of administration, such as tablets, coated tablets, solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings for example polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Syrups of the active ingredient according to the invention or combinations of active ingredients may additionally contain a sweetener, such as saccharin, cyclamate, glycerin or sugar, and/or taste improving agents such as flavourings e.g. vanillin or orange extract. They may also contain suspension agents or thickeners, such as sodium carboxymethyl cellulose, wetting agents, such as for example condensation products of fatty alcohols with ethylene oxide, or preservatives, such as p-hydroxybenzoates.

Injection solutions may, for example, be produced in the conventional manner, such as by the addition of preservation agents, such as p-hydroxybenzoates, or stabilizers, such as Complexons. The solutions are then filled into injection vials or ampoules.

Capsules containing one or several active ingredients may be produced for example by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Advantageously, the compositions may be formulated as dosage units, each unit being adapted to supply a fixed dose of active ingredient. Tablets, coated tablets, capsules, suppositories and ampoules are examples of suitable dosage unit forms. Each dosage unit preferably contains 5 to 100 n.mol of the said active ingredient and especially 15 to 50 n.mol of the said active ingredient.

As indicated above the new compounds may be administered to humans or other animal subjects. The optional dosage is in general proportional to surface area and will be in the range 5 to 50 n.mol/m² surface area/day. Thus for humans having a surface area of the order of 1.5 to 2.0 m², the optional daily dose will be in the range 7.5 to 100 n.mol/day. A course of treatment of 1 to 5 weeks for example about 3 weeks is appropriate. In general, administration is preferably by injection.

According to a still further feature of the present invention there is provided a method of inducing increased testosterone levels which comprises administering an effective amount of a pharmaceutical composition as hereinbefore defined to a subject whereby increased testosterone levels are induced.

Increased testosterone levels provide anabolic, i.e. growth-promoting, effects in humans and animals which are particularly useful in stock raising, for example in raising cattle, sheep and other domestic animals, including poultry.

The peptides may also be used to produce animal models which can be studied and used for therapeutic experiments.

A further major use of the new peptide, however, is in the production of material for immunological assay techniques. The peptide may then be covalently attached to a suitable high molecular carrier such as albumin, polylysine or polyproline in order to be injected into antibody-producing animal (e.g. rabbits, guinea pigs or goats). High specificity antisera are obtained by use of well known absorption techniques, using the high molecular carrier. By introducing radioactivity ($^{14}$C, $^{118}$O, $^{15}$N) into the peptide molecule, a radioammuno assay can readily be designed and used for determining the peptide in the different biological fluids such as serum (plasma), urine and cerebrospinal fluid.

In the Examples which are given by way of illustration only, deprotection by catalytic hydrogenation is effected using 10% palladium on carbon as the catalyst. The method of the Examples has been chosen so as to avoid side chain protection, thus simplifying the total experimental procedure.

In the Example the following abbreviations are used:
DCC—dicyclohexylcarbodiimide
DCU—Dicyclohexylurea
DME—dimethoxyethane
DMF—dimethylformamide
Gly—glycyl
Ser—L-seryl
pGlu—L-(pyro)glutamyl
OBzl—benzyl ester
OMe—methyl ester
HOSu—N-hydroxysuccincinide
EEDQ—N-ethoxycarbonyl-2-ethoxy-1,2-hydroquinoline
AcOH—acetic acid
ONB—p-nitrobenzyl ester
TEA—triethylamine
THF—tetrahydrofuran
p-TosOH—p-toluene sulphonic acid
Z—carbobenzoxy
Gel Silica Gel G
S1 $CH_2Cl_2$/MeOH (20:3)
S2 MeOH/Benzene (1:1)
S4 EtOH/$H_2O$ (7:3)
UV Ultra violet light—254 nm
N Ninhydrin
CT chlorine/o-tolidine
P Diazotized sulphanilic acid (Pauly's reagent)

The solvents used were pro analysi (p.a.) and were treated according to usual laboratory procedures before being used.

EXAMPLE 1

Synthetic Scheme

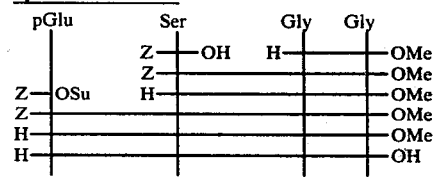

(a) L-Glycyl-Glycine methyl ester hydrochloride (H.Gly-Gly(OMe).HCl)

H.Gly-Gly(OMe).HCl was synthesized in a similar manner as described for H.Ser(OMe).HCl (Guttmann, S., and Boissonnas, R. A., Helv. Chem. Acta 41, 1852 (1958)):

Thionyl chloride (2.6 ml, 36 mmoles) was slowly added while stirring to methanol (10 ml) at about 10°–12° C. during 10–15 minutes. H.Gly-Gly(OH) (1.26 g 9.5 mmoles) was added and the temperature was kept at about 10° C. until complete dissolution was achieved. The temperature was then slowly raised to ambient temperature and the solution was stirred overnight.

The solvent was removed in vacuo, and the viscous residue was redissolved in a few mls of methanol and the solvent again evaporated. A quantitative yield (1.75 g) of crude product was obtained as white crystals. The crystals were dissolved in 90% ethanol and an equal volume of ethyl acetate was added. After standing at +4° C., 1.33 g (76%) of crystalline product was obtained. M.p. 121.5° C.

(b) Carbobenzoxy-L-seryl-Glycyl-Glycine methyl ester (Z-Ser-Gly-Gly(OMe))

Z-Ser-Gly-Gly(OMe) was synthesized in a similar manner as described for Z-Ser-Gly-Gly(OBzl) (Benoiton, L., and Rydon, H. N., J. Chem. Soc. 1960, 3328.

H-Gly-Gly(OMe).HCl (0.92 g, 5 mmoles) was dissolved in a mixture of CHCl₃ (20 ml) and CH₃CN (10 ml), and TEA (0.7 ml, 5 mmoles) was added. Z-Ser-(OH) (1.2 g, 5 mmoles) was and the mixture was cooled to 0° C. DCC (1.03 g, 5 mmoles) in CH₃CN (10 ml) was added dropwise, and the mixture was stirred overnight at ambient temperature. The mixture was filtered and the solvent evaporated in vacuo. The crude product was washed three times with warm ethylacetate and used without further purification in the subsequent reaction.

(c) L-seryl-Glycyl-Glycine methyl ester (H.Ser-Gly-Gly(OMe))

Z.Ser-Gly-Gly(OMe) (504 mg 1.36 mmoles) was dissolved in methanol (10 ml), a small amount of 10% Pd/C was added, and hydrogen gas was bubbled through the mixture for approximately 1 hour. TLC showed that the starting material had disappeared and that the product had formed (N+, CT+). The catalyst was filtered off, the solvent was evaporated and the product was used in the following reaction without further purification.

(d) Carbobenzoxy-L-(pyro)glutamyl-L-seryl-Glycyl-Glycine methyl ester (Z-pGlu-Ser-Gly-Gly(OMe))

The crude product of H.Ser-Gly-Gly(OMe) was dissolved in DMF (5 ml), and Z-pGlu(OSu) (50.7 mg, 1.4 mmoles) was added while stirring. Dioxan (10 ml) was then added and the mixture was stirred overnight. 324 mg of white, crystalline product was filtered off. M.p. 193° C. $R_f$(S 2)=0.56, UV+, CT+.

(e) L-(pyro)glutamyl-L-seryl-Glycyl-Glycine methyl ester (pGly-Ser-Gly-Gly(OMe))

Z-pGlu-Ser-Gly-Gly(OMe) (120 mg, 0.25 mmoles) was dissolved in a mixture of water (5 ml) and THF (5 ml), 10% Pd/C (100 mg) was added and hydrogen gas was bubbled through the solution for 60 minutes. The mixture was filtered, and the solvent was evaporated, yielding a quantitative amount of crude product. $R_f$(S 2)=0.34.

(f) L-(pyro)glutamyl-L-seryl-Glycyl-Glycine (pGlu-Ser-Gly-Gly(OH))

pGlu-Ser-Gly-Gly(OMe) (approximately 20 mg) was treated with 3-4 equivalents of aqueous NaOH for 1 hour. pH was then adjusted to 6 with 3 M aqueous HCl, and the mixture extracted with CH₂Cl₂ (2×1 ml) to remove unreacted ester. pH was then adjusted to approximately 2, and the solvent was evaporated in vacuo. The residue was extracted with methanol (2×2 ml), the solution was filtered, and the solvent was evaporated. The product was chromatographed on a Biogel P2 column (sold by Bio-Rad Laboratories, Calif., U.S.A.) and on elution with 0.5 M acetic acid has $R_f$(S 2)=0.25.

EXAMPLE 2

Synthetic Scheme

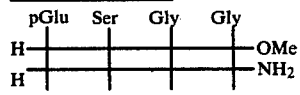

L-(pyro)glutamyl-L-seryl-Glycyl-Glycine amide (pGlu-Ser-Gly-Gly(NH₂))

pGlu-Ser-Gly-Gly(OMe) (approximately 45 mg, 0.12 mmoles of crude product from Example 1 (f) was dissolved in methanol (5 ml) and saturated with NH₃ gas at 0° C. The solution was left overnight at 0° C. The precipitated material was filtered off, yielding 25 mg (50%) of white crystalline product. Chromatography on Biogel P2, eluting with 0.5 M acetic acid gave $R_f$ (S 2)=0.12.

The following Pharmaceutical Examples are given by way of illustration only. The term "Peptide" refers to the peptide of formula (I) herein.

EXAMPLE A

Preparations for Subcutaneous Injection

Freeze-dried Peptide is filled into vials at two different concentrations.

Each vial contains:

| Peptide | 0.05 mg or 0.10 mg |
|---|---|
| Glycerine | 5.0 mg |

The contents of each vial are dissolved in 1 ml of isotonic sodium chloride for injection, prior to use.

EXAMPLE B

Tablets

Each tablet contains:

| Peptide | 0.1 mg |
|---|---|
| Maize starch | 24.0 mg |
| Lactose | 80.0 mg |
| Gelatin | 1.4 mg |
| Talc | 6.0 mg |
| Magnesium Stearate | 0.6 mg |

EXAMPLE C

Nasal Drop Solution on Spray

Each 1.0 ml of solution contains:

| Peptide | | 0.5 mg or 1.0 mg |
|---|---|---|
| Sodium Chloride | | 4.6 mg |
| NaH₂PO₄ . 2H₂O | | 4.2 mg |
| Na₂HPO₄ . 12H₂O | | 14.3 mg |
| Benzalkonium chloride | | 0.125 mg |
| Sterile water | ad | 1.0 ml |

One dose i.e. 2-3 drops (or equivalent spray) contains 0.05 mg or 0.10 mg Peptide.

EXAMPLE D

Suppositories

Each suppository contains:

| Peptide | 0.1 mg or 0.2 mg |
|---|---|
| Adeps solidus (Witepsol H.15) | 1.8 g |

EXAMPLE E

Suppositories

Each suppository contains:

| Peptide | 0.1 mg or 0.2 mg |
| Polyethylene glycol 1500 | 1.2 g or 1.1 g |
| Polyethylene glycol 3000 | 0.5 g |
| Distilled water | 100.0 mg |

EXAMPLE F

Rectal Solution

Content per rectiole:

| Peptide | 0.1 mg or 0.2 mg |
| Phenyl carbinol | 15.0 mg |
| Methyl cellulose | 40.0 mg |
| Sterile water | ad 2.0 ml |

We claim:

1. The compound of the formula:

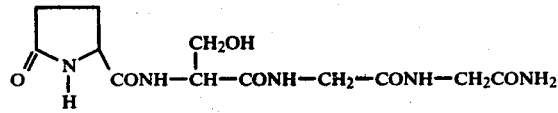

(I)

(wherein the pyroglutamyl and seryl moieties are of the L-series).

2. Pharmaceutical compositions comprising as active ingredient a testosterone-level-increase-enhancing amount of the compound of formula I as defined in claim 1 in association with a pharmaceutical excipient or diluent.

3. Compositions as claimed in claim 2 in the form of tablets, coated tablets, emulsions, powders, capsules, syrups, injection solutions or suppositories.

4. Pharmaceutical compositions in the form of dosage units wherein each dosage unit contains as active ingredient from 5 to 100 n.mols of a compound as defined in claim 1 in association with a pharmaceutical excipient or diluent.

5. Compositions as claimed in claim 4 wherein each dosage unit contains from 15 to 50 n.mols of active ingredient.

6. The composition as defined in claim 2 which is adapted for veterinary use.

7. A method of promoting growth of animal subject wherein an effective dose of the compound of claim 1 is administered to said subject.

8. The method as defined in claim 7 wherein the animal subject is a domestic animal.

9. A method for enhancing an increase in serum-testosterone-level in a human or animal subject which comprises administering a testosterone-level-increase-enhancing amount of the compound as defined in claim 1 to a human or animal subject.

10. A biochemical agent for use in immunological assay techniques comprising the compound of formula I as defined in claim 1 covalently attached to a high molecular carrier.

11. The biochemical agent as defined in claim 10 wherein the high molecular carrier is albumin, polylysine or polyproline.

* * * * *